United States Patent [19]
Canfield, II et al.

[11] Patent Number: 5,897,498
[45] Date of Patent: *Apr. 27, 1999

[54] ULTRASONIC DIAGNOSTIC IMAGING SYSTEM WITH ELECTRONIC MESSAGE COMMUNICATIONS CAPABILITY

[75] Inventors: Earl M. Canfield, II, Snohomish; Jens Ulrich Quistgaard, Seattle; Kenneth Dickerson, Lynnwood, all of Wash.; David Lauder, Lewistown, Pa.; Pascal Roncalez, Bellevue, Wash.; Michael A. Wood; David N. Roundhill, both of Bothell, Wash.

[73] Assignee: ATL Ultrasound, Inc., Bothell, Wash.

[*] Notice: This patent is subject to a terminal disclaimer.

[21] Appl. No.: 08/958,438

[22] Filed: Oct. 27, 1997

Related U.S. Application Data

[63] Continuation-in-part of application No. 08/719,360, Sep. 25, 1996, Pat. No. 5,715,823
[60] Provisional application No. 60/031,591, Nov. 21, 1996.

[51] Int. Cl.[6] ........................................... A61B 8/00
[52] U.S. Cl. ............................................... 600/437
[58] Field of Search .................................. 600/437, 407; 128/904, 903; 382/128, 130, 131, 132; 341/65; 705/3; 395/705

[56] References Cited

U.S. PATENT DOCUMENTS

| | | | |
|---|---|---|---|
| 4,958,283 | 9/1990 | Tawara et al. | 364/413.13 |
| 5,152,290 | 10/1992 | Freeland | 128/660.07 |
| 5,329,445 | 7/1994 | Mukai | 364/413.01 |
| 5,469,353 | 11/1995 | Pinsky et al. | 364/413.01 |
| 5,544,651 | 8/1996 | Wilk | 128/633 |
| 5,642,513 | 6/1997 | Schnellinger et al. | 395/705 |
| 5,655,084 | 8/1997 | Pinsky et al. | 705/3 |
| 5,680,129 | 10/1997 | Weinberger et al. | 341/65 |
| 5,734,739 | 3/1998 | Sheehan et al. | 382/128 |

FOREIGN PATENT DOCUMENTS

| | | | |
|---|---|---|---|
| 0 599 606 | 6/1994 | European Pat. Off. | G06F 11/22 |
| WO 95/15521 | 6/1995 | WIPO . | |

OTHER PUBLICATIONS

"Computer Design," vol. 35, No. 8, Jul. 1996 at pp. 112, 121–122.

*Primary Examiner*—George Manuel
*Attorney, Agent, or Firm*—W. Brinton Yorks, Jr.

[57] ABSTRACT

An ultrasonic diagnostic imaging system is provided which is capable of sending and receiving electronic messages directly from the user interface of the ultrasound system. This capability permits physicians to send messages, reminders, and diagnostic examination instructions directly to ultrasonographers using the system. The system operator is also able to call a physician to an ultrasound exam by means of an electronic message. Electronic messages can also be used to send and receive diagnostic reports and images, to retrieve diagnostic information such as the system presets for a particular type of ultrasonic examination, and to send and receive information from a hospital information system.

23 Claims, 3 Drawing Sheets

ULTRASONIC DIAGNOSTIC IMAGING SYSTEM WITH ELECTRONIC MESSAGE COMMUNICATIONS CAPABILITY

This application claims the benefit of U.S. Provisional Application No. 60/031,591, filed Nov. 21, 1996.

This application is a continuation in part of U.S. patent application Ser. No. 08/719,360, now U.S. Pat. No. 5,715,823 Sep. 25, 1996.

This invention relates to improvements in ultrasonic diagnostic imaging systems which can access data, images, messages, and other kinds of information from other ultrasound systems and information sources.

U.S. Pat. No. 5,715,823 describes an ultrasonic diagnostic imaging system with an HTTP server which enables the system to be accessed and transmit ultrasonic images and reports over the World Wide Web, enabling a physician to consult the diagnostic results stored on his ultrasound system from virtually any computer terminal in the world. This capability to access an ultrasound system and retrieve information and images from it may be characterized as "pull" technology, for the physician is "pulling" information out of the ultrasound system from a remote location. This contrasts with the "push" technology of prior art ultrasound networks, where the ultrasound system operator was required to affirmatively "push" information out of the ultrasound system and onto a network or frame grabber before the information could be transmitted or used external to the ultrasound system.

In addition to enabling remotely located users to access information from an ultrasound system, it would be desirable to provide the ultrasound system operator with the ability to access remotely located information and "pull" this information into the ultrasound system to aid in the ultrasound examination. For instance, a physician may be uncertain as to the nature of the pathology in a scanned ultrasound image. The physician may want to compare the acquired image with images of known pathological conditions. This would be facilitated by enabling the physician to recall a reference image from a library of images of known pathological conditions. Such a library may be located on the ultrasound system itself, on a local network to which the ultrasound system is connected, or at a remote location.

As another example, the ultrasound system operator may have a particular set of presets he or she prefers to use for a particular type of examination. These presets can initialize the setup of the ultrasound system for that type of examination, or perform a predetermined type of analysis such as an obstetrical measurement. The operator may have previously used the presets on another ultrasound system or stored them on a network storage device. It would be desirable to enable the operator to recall the presets from the other ultrasound system or storage location so that they can be automatically implemented for the current examination.

It would also be desirable to enable the ultrasound system operator to communicate directly with other physicians and locations. For instance, an ultrasonographer who has examined a patient may wish to call a diagnosing physician to review and make a diagnosis from ultrasound images which have just been acquired. It would be convenient for the ultrasonographer to be able to call the physician from the ultrasound system, either sending a message to the physician's office or contacting the physician immediately anywhere in the hospital.

It would also be desirable to enable the ultrasound system operator to have the ability to transmit acquired images or diagnostic reports directly from the ultrasound system to a physician at another location. This would make it possible, for instance, for a diagnosing physician to make an immediate diagnosis from the images and reports on the ultrasound system, and to communicate the diagnosis and its supporting images and reports directly to a referring physician, bringing more immediate attention to an ailing patient.

It would also be desirable to provide the ultrasound system operator with immediate access to the latest information about the ultrasound system and its capabilities. The operator should have immediate access to the most current information about ultrasound probes, system settings, and operating tips which enable the performance of the best ultrasound examination for any pathological condition. It should be possible for the manufacturer to deliver bulletins and reports with this type of information directly to the ultrasound system, and for the operator to quickly obtain this type of information if it is not present on the ultrasound system.

It would further be desirable for the ultrasound system operator to have direct access to other types of information on data bases in other areas of a hospital. Information about physicians and patients which is resident on a hospital information system should be accessible directly from the ultrasound system. It should also be possible for the hospital information system to acquire information directly from the ultrasound system, to determine information relating to ultrasound system utilization or for the preparation of patient records and statements, for instance.

In accordance with the principles of the present invention, an ultrasonic diagnostic imaging system incorporates electronic messaging functions which are operable from the user interface of the system. The electronic messaging capability makes it possible for the system operator to send messages including patient data to physicians at other locations, to call a physician to the examination room, or even to page physicians wherever they may be in the hospital or elsewhere. With electronic messaging the operator can retrieve presets for specific examinations from other ultrasound systems or storage locations.

Figure 1:
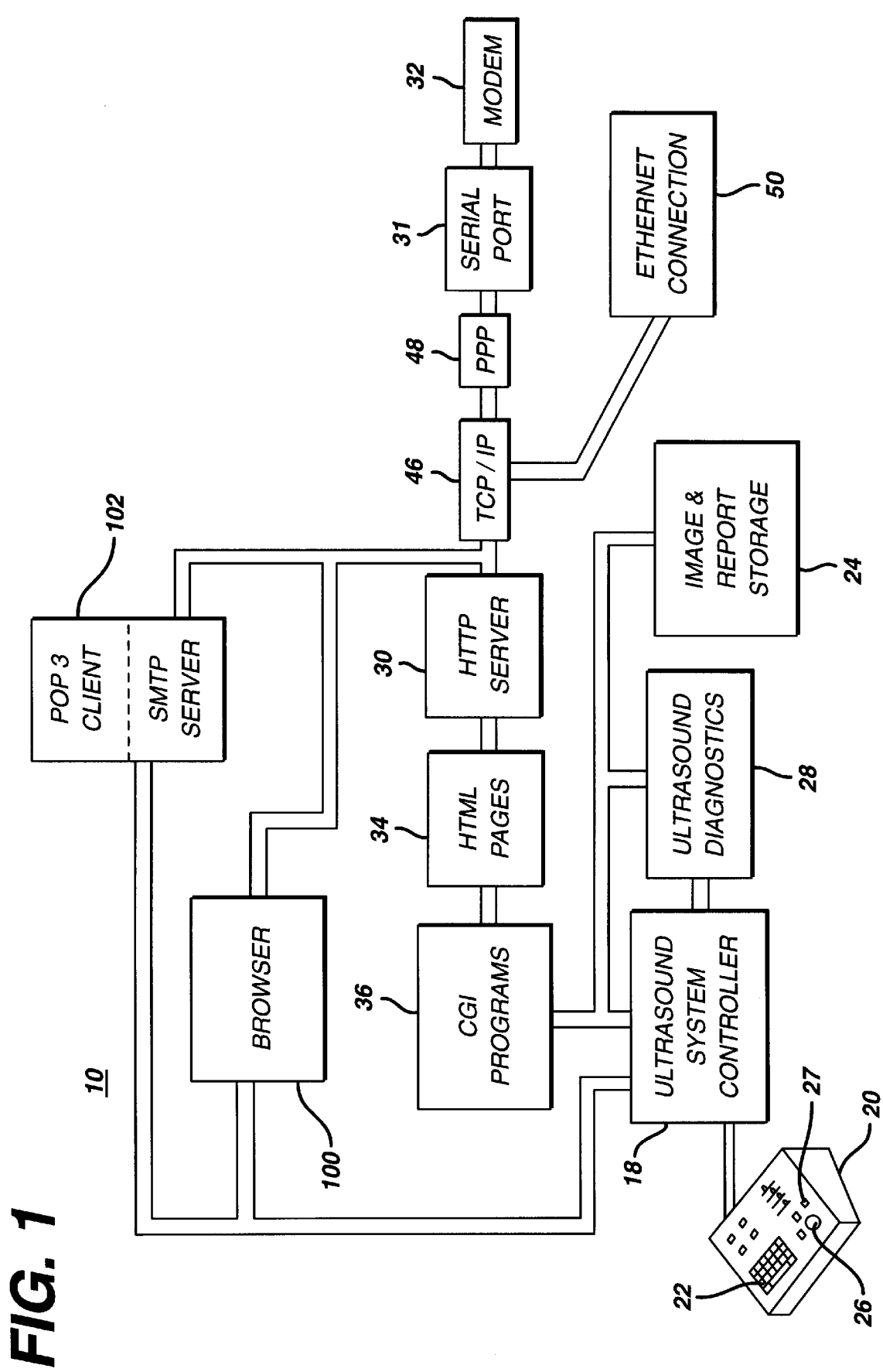
FIG. 1 illustrates in block diagram form an ultrasonic diagnostic imaging system with electronic messaging constructed in accordance with the principles of the present invention.
Figure 3:
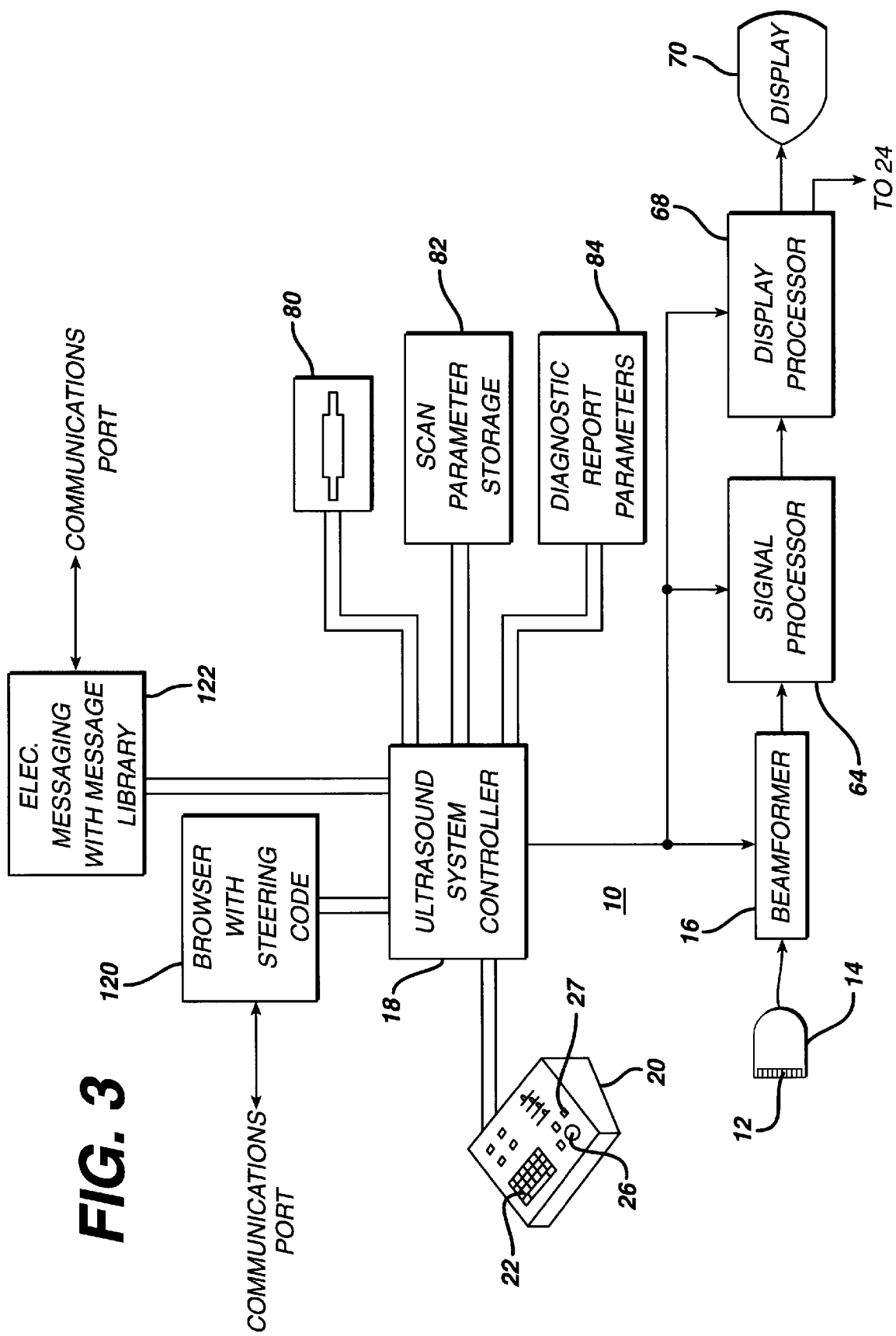
FIG. 3 illustrates in block diagram form the interaction of electronic messaging with the imaging and control elements of an ultrasonic diagnostic imaging system.

Referring to FIGS. 1 and 3, an ultrasonic diagnostic imaging system 10 constructed in accordance with the principles of the present invention is shown. The ultrasound system 10 includes a number of conventional components, including a scanhead 14 with an ultrasonic transducer 12 which transmits ultrasonic waves into the body of a patient, receives echoes returning from the interaction of the transmitted waves with internal organs and tissue of the body, and converts the received echoes into electrical echo signals. The electrical echo signals are appropriately delayed and combined by a beamformer 16 to form coherent beams of echo information. The beams of echo information are processed by a signal processor 64 in accordance with the type of diagnostic information which is to be obtained (e.g., B mode, Doppler, colorflow). The processed echo information is coupled to a display processor 68 to form ultrasonic images, which are stored in an image and report storage medium 24, displayed on a display 70, or both.

The operation of the ultrasound system 10 is under the control of a control panel 20, by which an operator sends control commands and otherwise interacts with an ultrasound system controller 18. The control panel 20 conventionally contains a number of user operable controls such as a keyboard 22, a trackball 26, and a Select Key 27. The controls of the control panel, together with video displayed controls with which the operator may interact (sometimes referred to as "soft keys") are referred to as the user interface. The operator may also manipulate the user interface to prepare diagnostic reports of the ultrasound exams performed, using a report generator software package which is conventionally stored in the ultrasound system or attached diagnostics module. The diagnostic reports may be displayed or printed out on a printer (not shown), and may also be stored in the image and report storage medium 24.

The ultrasound system 10 includes a HyperText Transfer Protocol (HTTP) server 30. The HTTP server 30 is connected to access ultrasonic images and reports from the storage medium 24, and makes the system's images and reports accessible to a personal computer, terminal, or workstation at a remote location. In FIG. 1 the server 30 is connected by a modem 32 to access an external or local communication network. The server 30 makes the diagnostic information of the ultrasound system 10 available to users connected to access the ultrasound system through a communication network, such as the network shown in FIG. 2.

The server 30 is connected to the modem 32 through a serial port 31. The modem 32 converts serial digital data from the serial port 31 into analog signals suitable for transmission over telephone lines. The modem also translates incoming analog telephone signals into digital data for passage through the serial port 31 and use by the ultrasound system. A suitable modem is available from Hayes Microcomputer Products, Inc., which has established standards used by a number of modem manufacturers.

Communication with the modem 32 is established by software known as PPP (point-to-point protocol) software as shown in block 48 of the drawing. PPP is a standard that enables multiple network protocols to be used over a modem line or other serial connection. Other standards can be used such as SLIP (Serial Line Internet Protocol), a standard that permits a communications protocol known as TCP/IP (discussed below) to be used over a modem line or other serial connection, or CSLIP (Compressed Serial Line Internet Protocol), a specialized form of SLIP. After the PPP software has been installed in the ultrasound system, it must be initialized or configured for the ultrasound system and modem with which it is operating. Configuration information controls the PPP software to be compatible with characteristics such as the serial port being used, the type of modem used, the phone line, host telephone number and dialing method, and login procedures and passwords. In general, the configuration information provides settings relating to initiating a network connection, when a connection is initiated, and what happens after a connection has been established. PPP software is incorporated in some operating system software packages such as Windows 95 from Microsoft Corporation of Redmond, Wash. for IBM-compatible PCs. PPP software for Apple personal computers is available from InterCon Systems Corporation of Herndon, Va., among others.

Communicating with the PPP software is a network protocol called the TCP/IP Internet Protocol Suite. TCP/IP is named after its two most commonly used protocols, the Internet Protocol (IP) and the Transmission Control Protocol (TCP). The IP protocol controls the routing of data and the TCP protocol controls the transfer of data. TCP/IP provides a common means of interconnection through packet transfer devices known as gateways. A gateway is a specialized internetworking computer that connects two or more networks and routes packets of data between them.

When the ultrasound system has data it wishes to transfer over the Internet or other network, the data is passed to TCP/IP as shown in block 46 of the drawing. TCP encapsulates data into segments called TCP packets with header information that is used to track, check and order the data segments in the proper sequence. Since a block of data is transmitted over the Internet in discrete packets, individual ones of which may be routed differently by gateways, there is no assurance that the packets will arrive at their destination in the proper order or without errors. The TCP packets provide a means of assuring packet delivery, integrity, and sorting order. At the receiving end the packets are checked for errors in accordance with the TCP packet header information, error-free segments are acknowledged, and the packets are put in order to reassemble the original block of data. The sender keeps track of segment acknowledgments, and if a segment is not timely acknowledged the sender retransmits the packet. If a segment is lost on initial transmission or received out of order, TCP holds the received segments until all segments are accounted for at the received end, at which time they may be ordered in their proper and complete sequence for reassembly of the original block of data.

At the transmitting end, TCP packets are passed to IP, which puts the segments into the form of IP packets or datagrams. The datagram contains an IP header which provides addressing information used by gateways to route the datagram to its proper destination. The IP header contains the source and destination Internet addresses to enable gateways to properly route the data, and the receiver to acknowledge receipt of the datagram. IP makes a best-effort attempt to deliver all datagrams, but does not assure their delivery. Assurance of delivery is provided by TCP through acknowledgment and retransmission as described above.

Like the PPP software, the TCP/IP needs to be configured for the particular ultrasound system and its environment. Typical configuration information for TCP/IP includes information on the type of local network if the ultrasound system is locally networked with other ultrasound machines (e.g., Ethernet or token ring network), information as to the addresses of other systems on the local network, the gateway address if the system is performing a router function, the user name of the ultrasound machine and access password, the address of the servers on the ultrasound system, the Internet address (IP address) for the ultrasound system, and the default domain for the local network. Like PPP, TCP/IP software also comes with some system software packages such as Windows 95, and is available for Apple computers from InterCon.

In FIG. 1 TCP/IP is connected to a local network medium, in this case an Ethernet connection 50. The Ethernet connection 50 connects the ultrasound system to other systems on a local network. The traditional Ethernet network uses a linear bus with carrier sense multiple access with collision detection (CSMA/CD). It is sometimes described by a similar standard that uses an alternate frame format under IEEE 802.3. The Ethernet connection 50 may be used to access local area networks (LANs), wide area networks (WANs), IEEE 802.5 token rings, or other networking infrastructures. Data can be transmitted on an Ethernet network at high speed (previously 10 Megabits per second; current versions have speeds of up to 100 Megabits per second), with each system permitted to transmit only when no other system is currently transmitting over the system.

Interacting with the TCP/IP and PPP network software is the HTTP server 30. The HTTP server is a software program with which a Web browser communicates to access information from the ultrasound system. The HTTP server responds to internal or external requests by displaying Web pages of information and hypertext connections to additional Web pages and information such as ultrasound images and reports. The HTTP server also responds to external requests to perform a specific action associated with a button or control on the ultrasound system, as described more fully in the parent application.

In response to external requests the HTTP server 30 transmits HyperText Markup Language (HTML) pages 34 to an inquiring Web browser. HTML pages describe what the Web browser will display on the screen at the remote terminal, including buttons, text, images, animated real time loops of images, sounds, and so forth. HTML pages may be directly encoded in software by following the instruction published in a number of reference texts such as *HTML and CGI Unleashed*, by John December and Mark Ginsburg, published by Sams.net Publishing, Indianapolis, Ind. Simple HTML pages may be written using commercially available desk-top publishing and word processing software, then encoded in HTML form using software known as the Internet Assistant or functionally similar software, which may be downloaded through Microsoft's homepage at www.microsoft.com. Alternatively, public domain software known as "Webmaker" may be downloaded from the Internet and used to make Web pages. Web pages contain HTML tags of data which describe how the page is to be interpreted by a Web browser. Links to ultrasound image files are provided by IMG tags in the Web page code. An HREF hypertext reference provides a means for linking to other Web pages on the same ultrasound machine, or to Web pages on any other host machine on the network or Web. Once the HTML pages are created they are copied to the ultrasound machine and their storage addresses provided to the HTTP server. Whenever a remote terminal or browser asks to view a particular Web page of the ultrasound machine, the HTTP server 30 is responsible for finding the page and sending its contents back to the requester.

The ultrasound system 10 includes a number of small executable programs called Common Gateway Interface (CGI) programs as shown at 36. The CGI programs provide an interface between the HTML pages and the hardware and software of the ultrasound system. The CGI programs communicate with the ultrasound system, asking the system to perform actions or provide requested information such as images, reports, or current status. In a constructed embodiment the CGI programs respond to requests for information by dynamically creating custom HTML pages in which the requested information is embedded. The parent application illustrates the operation of CGI programs that provide patient directories of ultrasound images and reports, display of a selected ultrasound image, general purpose programs that execute tasks in response to input arguments, perform system diagnostics, and provide patient directories for a number of ultrasound machines on a network. The CGI programs in a constructed embodiment are stored on the ultrasound system's hard disk in a directory called "cgi-bin." In performing their operations the CGI programs access ultrasound images and reports which are stored at 24, accesses and executes diagnostic routines stored at 28, and interacts with the controls of the ultrasound system through the ultrasound system controller 18.

Alternatively, small program fragments can be embedded in the server code and caused to execute based on CGI transactions.

In accordance with the principles of the present invention, the ultrasound system 10 includes a simple mail transfer protocol (SMTP) server 102. The SMTP server 102 sends and receives electronic messages by way of TCP/IP 46 over a local network or the Internet through a network connection such as Ethernet connection 50 or modem 32. The SMTP server is connected to the ultrasound system controller 18 so as to interact with the ultrasound system storage media, user interface, and display. Software programs such as the Eudora electronic messaging program, which includes a POP3 client protocol for electronic message reception and SMTP for transmission, can be employed, with the POP3 client used to periodically poll a host system for received messages. The SMTP server 102 receives electronic messages and displays a notice on the system display 70 by way of the system controller 18 when messages have been received by the ultrasound system 10. The messages can then be accessed through the user interface using the keyboard 22, trackball 26, or Select Key 27 and shown on the system display 70.

In general, the POP3 client is used when another system functions as the host system for message transmission and reception (POP host), and a full SMTP server implementation is used for permanent Ethernet connections. Messaging can also be performed by the HTTP server 30, which can deliver messages by HTML pages and the HTTP protocol to other locations.

The electronic messaging capability provided by the SMTP server 102 can benefit the ultrasound system operator in a number of ways. The electronic messages can attach any of the information stored on the ultrasound system for transmission to interested parties, such as ultrasound images, reports (or individual calculations), ultrasound image loops, system presets, user entered OB charts or formulas, system error logs, or any other information resident on the ultrasound system. Likewise, the operator can receive such information from other locations and use it on the ultrasound system.

The ability to send electronic messages from the ultrasound system allows the operator to easily consult with others quickly. Physicians at other locations can send messages to the ultrasound system which pertain to future exams to be performed on the system, providing reminders and important information which can guide an ultrasound exam. The ability to send or retrieve system presets for a given exam enables the same exam to be performed on ultrasound systems at other locations automatically, without having to manually set up a machine to try to duplicate an exam done elsewhere. An ultrasonographer who uses numerous ultrasound machines at different locations can store his or her preferred system presets in a file on the ultrasound system or network server, which can then be referenced in an electronic message or from an HTML page, and retrieved over the Internet or network for use wherever the ultrasonographer happens to be performing ultrasound exams that day. The browser can be used to download new or specialized user setups from the system manufacturer, and users can exchange system setups by way of electronic messaging. Similarly, specialized or preferred diagnostic tools such as preferred OB tables or OB tables designed for a particular culture or country can be downloaded from a remote location.

In accordance with a further aspect of the present invention, the ultrasound system 10 includes a browser 100 which can communicate by way of hypertext links with other sites (such as other ultrasound systems, servers and terminals) which have information of interest to the ultrasound system user. The browser 100 comprises software which enables the ultrasound system operator to view hypertext documents (HTML pages) stored on a server remote from the ultrasound system or on the ultrasound system itself. The browser 100 is connected to the ultrasound system controller 18 so as to interact with the ultrasound system storage media and display, and to be operable by means of the user interface of the ultrasound system. To "click" on a hypertext link of a displayed HTML page, for instance, the user manipulates a cursor on the browser display with the trackball 26 or keys of the keyboard 22, then selects the desired information with the Select Key 27 or the Enter key of the keyboard. Browser software such as that which is available from Netscape Communications Corporation of Mountain View, Calif. or the Internet Explorer browser available from Microsoft Corporation conveniently enable the ultrasound system operator to obtain images, reports, and other information over a local network or the World Wide Web of the Internet.

FIG. 3 illustrates further details of the operation of these capabilities. In this embodiment the browser 120 is compiled with software code which steers received system preset data to the appropriate storage area of the ultrasound system, where it can be utilized by the ultrasound system controller to control the functioning of the system. When the operator uses the browser to access system preset data from another ultrasound system or data storage device, the steering code directs the received system preset data to scan parameter storage 82, where it is stored as custom preset data. Alternatively, the operator may download the custom preset data directly to scan parameter storage 82 using the File Transfer Protocol FTP. When the operator is given the choice to select system setup parameters at the beginning of an imaging procedure, the operator manipulates the user controls to select this custom preset data rather than the standard preset data for the procedure (sometimes referred to as "Tissue Specific Imaging™" setups) that is stored on the ultrasound system. The ultrasound system controller 18 will then initialize the ultrasound system to perform ultrasonic scanning in accordance with the operator's custom system presets, as indicated by the connections between the ultrasound system controller 18 and the beamformer 16, signal processor 64, and display processor 68 of the ultrasound system.

As another example, suppose that the operator wishes to use a gestational age table designed specifically for a particular nationality, rather than one of the gestational age tables installed on the ultrasound system. The system operator uses the browser 120 to acquire the desired gestational age table from outside the ultrasound system and the steering code software stores the table in the diagnostic report parameters storage medium 84 as a custom OB table. When the operator is given an opportunity to select a gestational age table for estimating fetal age, the "custom table" option is selected, and the ultrasound system controller causes the fetal age to be estimated using the gestational age table imported by the system operator.

Sending ultrasound image loops to other physicians enables a physician at a remote location to participate in or make the diagnosis by viewing the real time image loop that was acquired elsewhere. For referring physicians, the diagnosing physician can image a patient and prepare a report on the ultrasound system, then send the images and report as an electronic message or message attachment directly to the referring physician from the ultrasound system using the system's electronic messaging capability.

Electronic messaging from the ultrasound system is useful in analyzing problems and questions of system performance. The ultrasound system operator can send the system error log to the system manufacturer, even accompanied by images acquired at the time of a problem, to enable the manufacturer to remotely diagnose system performance problems. This greatly aids in isolating obscure problems which happen aperiodically or only at certain locations, since the manufacturer can receive system data immediately at the time the problem arises.

The electronic messaging system can be configured to automatically capture system information when a problem occurs, such as the system error log, status and configuration, and to automatically send the error log to the manufacturer or repairman at the time of the problem. The manufacturer or repairman can review these messages and their information as they are received, and can notify the system operator if the information indicates that repairs or adjustments are needed to the ultrasound system. The manufacturer can contact the ultrasound system operator by return electronic message or other medium to request additional information if such appears warranted or useful.

With each ultrasound system having its own electronic mailbox, the manufacturer can quickly and easily transmit bulletins about the system directly to the system mailbox. Information on new applications, diagnostic tips, or setups can be sent by the manufacturer to its various types of ultrasound systems (e.g., premium, midrange, cardiology, general imaging, digital, etc.) and used to improve previous applications or to perform new ones.

In a preferred embodiment, each ultrasound system has its own unique electronic message address for the sending and receipt of electronic messages. It is preferable to relate the serial number of an ultrasound system to the system's unique electronic mailbox address, for instance, for quick and unique identification of an ultrasound system and its mailbox. The electronic mailbox is password protected so that access to messages is limited to only those to whom the owner of the ultrasound system has granted access permission. The data on the ultrasound system can be edited for security before transmission such as by deleting the name of the patient before transmission of images and reports. Higher concerns for security can be addressed by encrypting data before transmission.

The browser 100 permits the ultrasound system operator to access information about other ultrasound practitioners, enabling physicians to exchange ultrasound system electronic mail addresses with their colleagues, for instance, which can lead to further exchanges of diagnostic information and other communications. The system manufacturer can organize a Web page, for instance, where system users can post their system addresses and other information they want to make public among their peers.

Electronic messaging can aid a hospital in determining user exam demographics and utilization. For instance, the ultrasound system controller can be programmed to identify patient demographics and reports meeting certain criteria, such as women over age 40 who are undergoing an OB exam. At the conclusion of the exam the exam report and images are automatically sent by electronic message to a central site in the hospital such as a hospital information system where such demographics are kept or studies are being made of exams of that type, using prepared messages stored in the message library 122. The exams could also be automatically sent to the hospital specialist in that area of practice, such as a perinatologist specializing in pregnancies of women over age 40. Another useful feature to help a hospital manage its ultrasound resources is the automatic transmission to hospital administration each day or week of an electronic message containing the number of exams performed on the ultrasound system that day or week and the length of time required for each exam, enabling a hospital administrator to update patient records and statements. Again, this may be done by means of a previously prepared message stored in the message library 122. Alternatively, a CGI program can create an HTML page periodically with the desired information in it, and the page can be accessed by the browser of a hospital administrator when the data is needed.

Another use of the electronic messaging capability is to page physicians on call. In a constructed embodiment, depressing a button on the ultrasound system causes the system to send a previously prepared electronic message by modem 32 or network modem to a pager service in the format used by the pager service. The message received by the pager service identifies the telephone number of the pager, and gives a message to be sent to an alphanumeric pager, such as "Call Exam Room 7 Re: Ultrasound Exam." Upon receipt of the message the pager service sends the message to the pager of the physician who is on call in the hospital. The message may identify the ultrasound system and can also ask the physician to call the system operator to assist in or make a difficult diagnosis, for instance. This capability enables an ultrasonographer to quickly contact a reading physician when critical diagnostic decisions are needed.

The browser 100 enables the ultrasound system operator to access a remote library of baseline comparative ultrasound images in his or her practice. Such ultrasound image libraries can be compiled by system manufacturers, universities, professional organizations, large hospitals and clinics and others. The image library can be resident at other sites on the Internet or network, or may be locally available on a connected server, CD-ROM, or even the system's hard disk. If a physician is imaging pathology which is unfamiliar to the physician, the physician can access the image library through the browser 100. Reference images from the library can be called up and displayed on the ultrasound system monitor side by side along with the patient's pathology, enabling comparisons to be made which can aid in diagnosis.

Figure 2:
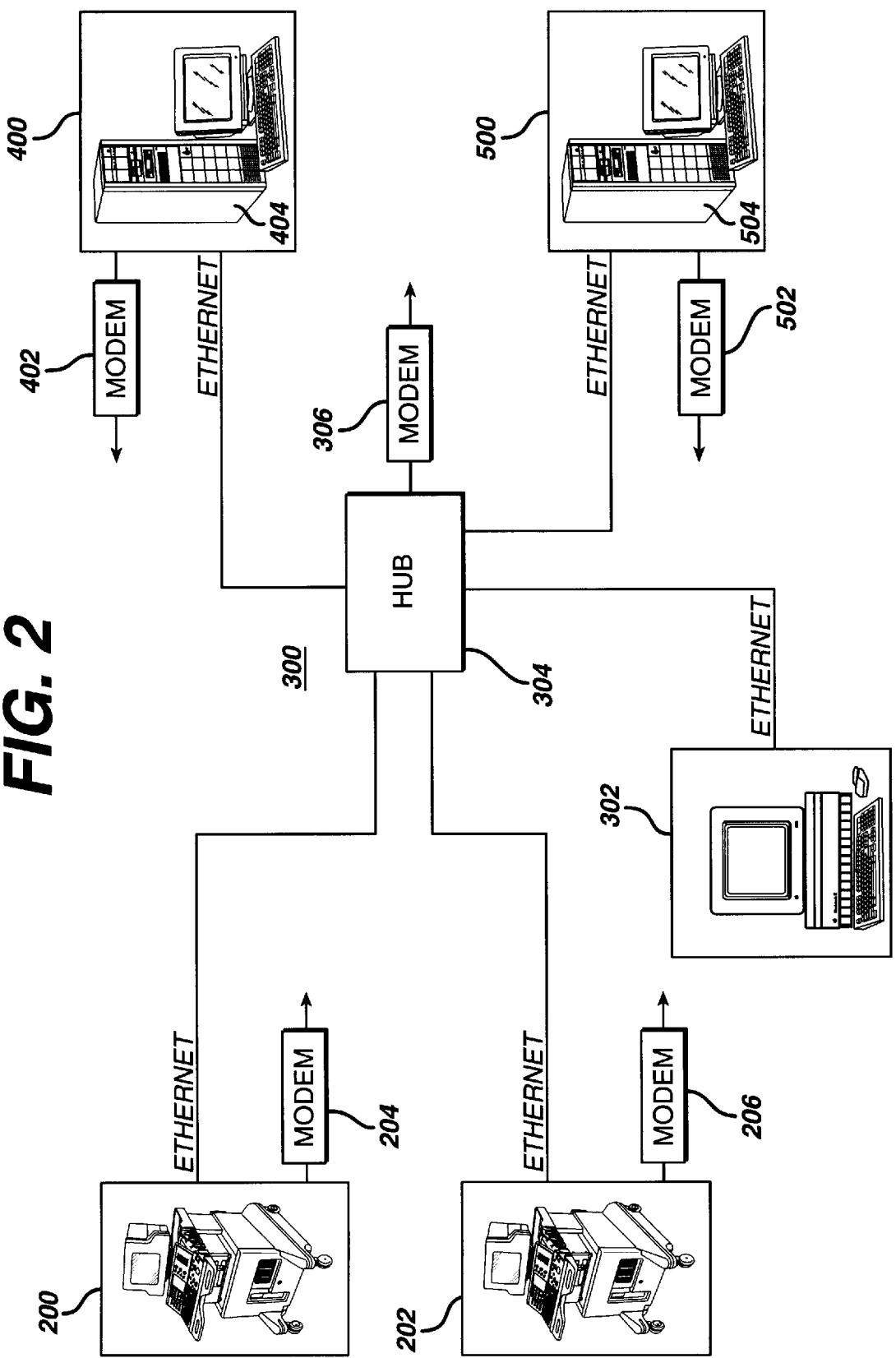
FIG. 2 illustrates a network by which ultrasound systems have access to a library of reference images and a hospital information system.

Such a capability is shown in FIG. 2, which shows two ultrasound systems 200 and 202 connected to a hub 304 of an Ethernet network 300. Also connected to the hub 304 is the terminal or workstation 302 of a network administrator, a reference image library 400 which includes a server 404, and a hospital information system (HIS) or radiology information system (RIS) 500 with a server 504. Each system on the network has a modem for connecting to other information sources, and the network also has a network modem 306 for communications into and out of the network 300.

In the example of FIG. 2, the reference image library 400 is available to both of the ultrasound systems 200 and 202 which are connected to the network 300, and other systems may access the reference image library 400 by way of the library modem 402 or the network modem 306. The library may be password protected to allow access only to users giving approved passwords. When accessed, the library 400 presents HTML pages with different exam categories, such as obstetrical, abdominal, cardiology, etc., on the browser of the user. Picking an exam category branches the operator to more detailed hierarchies of exams, pathologies, and conditions, or an operator can simply type in a string of identifiers to take him directly to the type of images sought, such as "obstetrical-fetal-head-trimester 3". In this manner the library user follows an ever narrowing focus of choices until an image of the desired pathology or condition is found, or directly access the type of images needed. The ultrasound system operator pulls the desired ultrasound image into the ultrasound system, where it can be copied and pasted, either manually or automatically, on the display 70 alongside an ultrasound image of a patient. The operator can compare the patient's image with the reference image from the library to aid in making a diagnosis of the patient's condition.

It is also possible to store a local reference image library on the ultrasound system for access by the system's browser as described above. The reference image library can be stored on any medium of the ultrasound system that is accessible to the browser. In FIG. 1 the reference image library can be stored on a device which is a part of storage medium 24, enabling the browser 100 to access the reference image library by logging onto the server 30. In the example of FIG. 3, the reference image library is stored on a removable magneto-optical disk which is used on an M-O drive 80. By locating the library on removable disk media, a new or updated library of images can be loaded onto the system at any time. As before, the browser 120 is used to access the image library on the ultrasound system through the server, and a branching path of choices is followed or an image type directly accessed, leading to the desired reference image. The reference image is then used as a comparative image to aid in making a diagnosis from images obtained by the ultrasound system. The ability to display reference images on the system is also useful in the training of new ultrasound system users.

The browser 100 has a number of other uses which are important to the ultrasound practitioner. The system user can use the browser 100 to view ultrasound images previously stored on the system. The browser does this in the same manner as inquiries by external terminals, by logging onto the server 30 to display the system's patient image directory on the system monitor 70. By connecting to remote sites by means of the modem 32 or network connection 50 the browser can be operated to send images and reports to a remote location. The browser can also be used to access hospital and radiology information systems 500 within the hospital or network to view lab reports, physician schedules, and the like.

The browser 100 can be used for training and operation information retrieval. Useful tips, system "help" messages, and even the operator's manual for the ultrasound system can be stored electronically on the system such as on disk or a CD-ROM and can be accessed through the browser 100 to guide the operator in using the ultrasound system.

What is claimed is:

1. A medical diagnostic ultrasound system which produces and stores diagnostic ultrasound images or diagnostic reports, comprising:

electronic message software installed on said ultrasound system; and means for connecting said electronic message software to send or receive electronic messages to or from sources external to said ultrasound system.

2. The medical diagnostic ultrasound system of claim 1, further comprising means for connecting said electronic message software to a network, whereby said ultrasound system can send or receive electronic messages over said network.

3. The medical diagnostic ultrasound system of claim 2, wherein said means for connecting said electronic message software to a network further comprises TCP/IP software.

4. The medical diagnostic ultrasound system of claim 3, wherein said means for connecting said electronic message software to a network further comprises PPP software.

5. The medical diagnostic ultrasound system of claim 4, wherein said means for connecting said electronic message software to a network further comprises a modem.

6. The medical diagnostic ultrasound system of claim 1, wherein said ultrasound system further comprises a user interface for controlling the operation of said ultrasound system,
wherein said electronic message software is also operated by said user interface.

7. The medical diagnostic ultrasound system of claim 6, wherein said user interface includes an image display.

8. The medical diagnostic ultrasound system of claim 6, wherein said user interface includes a keyboard.

9. The medical diagnostic ultrasound system of claim 6, wherein said user interface includes a trackball.

10. The medical diagnostic ultrasound system of claim 1, further comprising:
a library of electronically stored reference ultrasound images connected to said ultrasound system; and
means for displaying said reference images on the display of said ultrasound system.

11. The medical diagnostic ultrasound system of claim 1, further comprising:
browser software installed on said ultrasound system; and
means for connecting said browser software to a database external to said ultrasound system,
whereby externally stored images or information are remotely accessible through said browser software.

12. The medical diagnostic ultrasound system of claim 11, wherein said ultrasound system further comprises a user interface for controlling the operation of said ultrasound system,
wherein said browser software is also operated by said user interface.

13. The medical diagnostic ultrasound system of claim 1, further comprising:
browser software installed on said ultrasound system; and
means for connecting said browser software to a source of reference images external to said ultrasound system,
whereby externally stored reference images are remotely accessible through said browser software.

14. The medical diagnostic ultrasound system of claim 1, wherein said electronic message software comprises means for sending a page,
whereby individuals may be paged from said ultrasound system.

15. The medical diagnostic ultrasound system of claim 14, wherein said electronic message software comprises means for sending an electronic message to a paging service.

16. The medical diagnostic ultrasound system of claim 15, wherein said means for sending an electronic message comprises means for sending a message in a format designed for sending a paging message to a paging service.

17. The medical diagnostic ultrasound system of claim 14, further comprising means for storing prepared paging messages,
wherein a prepared paging message may selected by a user for transmission by said electronic message software.

18. The medical diagnostic ultrasound system of claim 1, wherein said means for connecting comprises means for connecting said electronic message software to a hospital information system,
wherein electronic messages may be sent over said hospital information system by said electronic message software.

19. The medical diagnostic ultrasound system of claim 18, wherein said electronic messages comprise information concerning usage of said ultrasound system.

20. The medical diagnostic ultrasound system of claim 19, wherein said electronic messages comprise information for patient records or statements.

21. The medical diagnostic ultrasound system of claim 1, wherein said means for connecting comprises means for connecting said electronic message software to a network,
wherein information regarding use of said ultrasound system may be sent to a system operator over said network.

22. The medical diagnostic ultrasound system of claim 21, wherein said information comprises information useful in the conduct of an ultrasound examination of a patient.

23. The medical diagnostic ultrasound system of claim 21, wherein said information comprises system setup information.

* * * * *